US010232954B2

(12) United States Patent
Siegmeth et al.

(10) Patent No.: US 10,232,954 B2
(45) Date of Patent: Mar. 19, 2019

(54) APPARATUSES AND METHODS FOR REDUCING OZONE CREATION FROM ULTRAVIOLET (UV) LIGHT

(71) Applicant: The Boeing Company, Chicago, IL (US)

(72) Inventors: Jeff Siegmeth, Chicago, IL (US); Karen Hills, Chicago, IL (US); Jamie Childress, Mercer Island, WA (US); Douglas Brown, Chicago, IL (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 15/271,349

(22) Filed: Sep. 21, 2016

(65) Prior Publication Data

US 2018/0079528 A1 Mar. 22, 2018

(51) Int. Cl.

| | |
|---|---|
| ***B64D 47/02*** | (2006.01) |
| ***A61L 2/10*** | (2006.01) |
| ***A61L 2/26*** | (2006.01) |
| ***B64D 11/00*** | (2006.01) |

(52) U.S. Cl.

CPC ................ *B64D 47/02* (2013.01); *A61L 2/10* (2013.01); *A61L 2/26* (2013.01); *B64D 11/00* (2013.01); *A61L 2202/11* (2013.01); *A61L 2202/14* (2013.01); *A61L 2202/25* (2013.01)

(58) Field of Classification Search

CPC .............. B64D 47/02; A61L 2/10; A61L 2/26

See application file for complete search history.

(56) References Cited

U.S. PATENT DOCUMENTS

| | | | | |
|---|---|---|---|---|
| 8,940,229 B2 * | 1/2015 | Halfmann et al. | A61L 2/10 | 422/22 |
| 2004/0120844 A1 * | 6/2004 | Tribelsky et al. | A01N 1/00 | 422/2 |
| 2016/0008498 A1 * | 1/2016 | Boysset et al. | A61L 2/10 | |

* cited by examiner

*Primary Examiner* — Regina M Yoo

(74) *Attorney, Agent, or Firm* — McDonnell Boehnen Hulbert & Berghoff LLP

(57) ABSTRACT

Apparatuses and methods are described for use of an ultraviolet (UV) light source, such as in a cleaning device, in which ozone creation due to reaction of the UV light with oxygen in the air is reduced. An example method includes dispersing, by a gas outlet, oxygen-depleted gas over a UV light source, and directing UV light from the UV light source to pass through the oxygen-depleted gas onto an area. An example apparatus includes a UV light source to direct UV light onto an area, and a gas outlet to disperse oxygen-depleted gas over the UV light source, such that the UV light passes through the oxygen-depleted gas onto the area.

18 Claims, 6 Drawing Sheets

200 ─┐

START

↓

DISPERSING, BY A GAS OUTLET, OXYGEN-DEPLETED GAS OVER AN ULTRAVIOLET (UV) LIGHT SOURCE

╲─202

↓

DIRECTING UV LIGHT FROM THE UV LIGHT SOURCE TO PASS THROUGH THE OXYGEN-DEPLETED GAS ONTO AN AREA

╲─204

↓

END

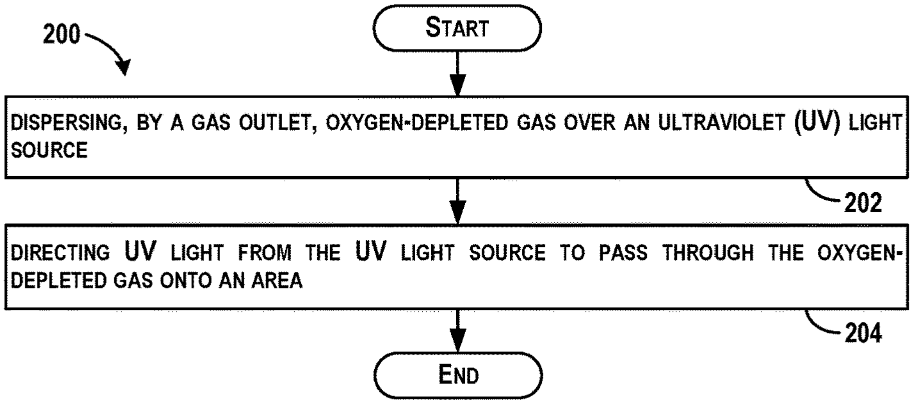

DISPERSING THE OXYGEN-DEPLETED GAS OVER THE UV LIGHT SOURCE FOR A PREDETERMINED TIME PERIOD PRIOR TO OPERATION OF THE UV LIGHT SOURCE TO DIRECT THE UV LIGHT ONTO THE AREA

╲─206

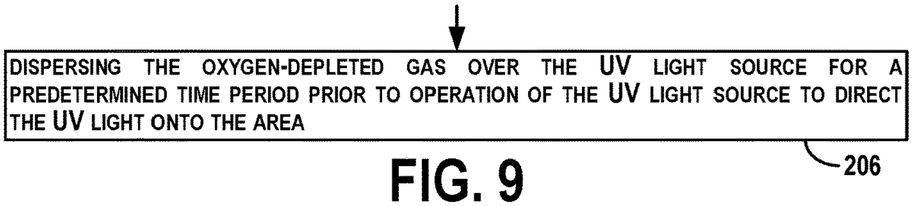

CAPTURING, BY A GAS INLET, DISPERSED OXYGEN-DEPLETED GAS INTO A CONTAINER

╲─208

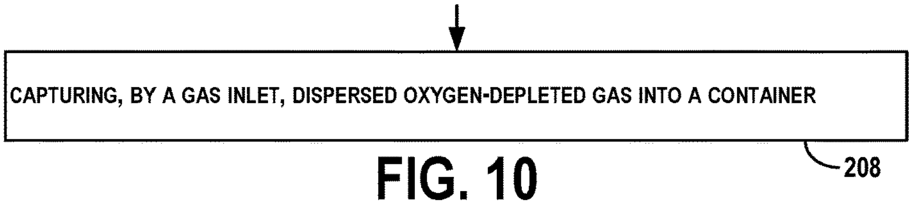

OPERATING THE UV LIGHT SOURCE TO EMIT UV LIGHT ONTO THE AREA WHEN THE LAVATORY IS NOT IN USE

╲─210

↓

DISPERSING THE OXYGEN-DEPLETED GAS OVER THE AREA SO AS TO DISPLACE AIR THAT IS IN A PATH OF THE UV LIGHT WHILE THE UV LIGHT SOURCE IS EMITTING THE UV LIGHT

╲─212

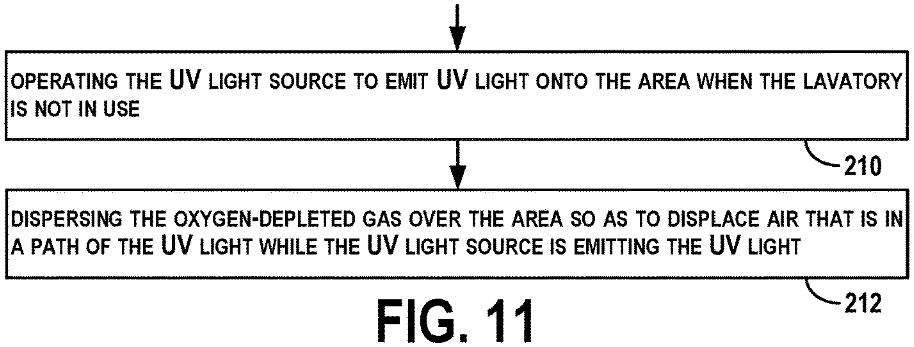

DISPLACING AIR OVER THE AREA TO MITIGATE FORMATION OF OZONE GAS DUE TO THE UV LIGHT REACTING WITH OXYGEN IN THE AIR

╲─214

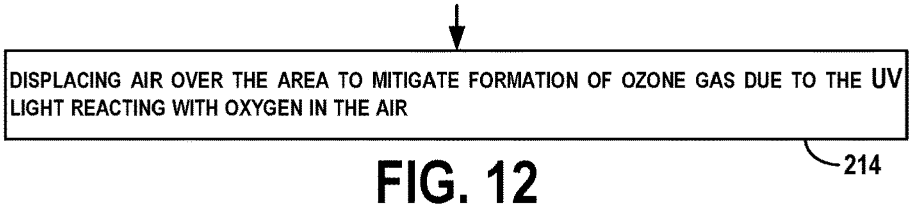

FIG. 12

APPARATUSES AND METHODS FOR REDUCING OZONE CREATION FROM ULTRAVIOLET (UV) LIGHT

FIELD

The present disclosure relates generally to systems and methods for reducing ozone creation from use of ultraviolet (UV) light sources, and more particularly to, reduce creation of ozone by temporarily displacing oxygen filled air in a path of the UV light source while the UV light source is emitting light such that the light passes through substantially oxygen-depleted gas rather than ambient air, and therefore, reduces an opportunity for the creation of ozone.

BACKGROUND

Ultraviolet (UV) light is effective as a disinfection method by using short-wavelength UV light to kill or inactivate microorganisms. UV light can be used in a variety of cleaning applications, such as food, air, and water purification, as well as in medical sanitation and sterile work facilities.

When using a UV light source in ambient air, certain wavelengths of UV light (particularly the Far UV wavelengths such as between 100-200 nm) can cause oxygen in air to react and become ozone (O3). Thus, ozone gas is often generated when air is exposed to UV light.

For UV light source cleaners used in proximity to humans, ozone gas generation is undesirable. Existing solutions to mitigate ozone gas include use of ozone scrubbers. Other solutions include increased ventilation of ozone gas generated from exposure to UV light, such as in instances in which the UV light source cleaner is used in an enclosed area. However, these solutions only consider mitigation of ozone, and do not prevent creation of ozone altogether, which may be more effective as UV light cleansing becomes more commonplace.

Thus, improved UV light cleaning devices are needed that increase safety and air quality, as well as remove undesirable ozone smell.

SUMMARY

In one example, a method is described comprising dispersing, by a gas outlet, oxygen-depleted gas over an ultraviolet (UV) light source. The method also includes directing UV light from the UV light source to pass through the oxygen-depleted gas onto an area.

In another example, another method is described comprising dispersing, by a gas outlet, an inert gas over an ultraviolet (UV) light source for a predetermined time period prior to operation of the UV light source, and after the predetermined time period, operating the UV light source to direct the UV light to pass through the inert gas onto an area.

In still another example, an apparatus is described comprising an ultraviolet (UV) light source to direct UV light onto an area, and a gas outlet to disperse oxygen-depleted gas over the UV light source, such that the UV light passes through the oxygen-depleted gas onto the area.

The features, functions, and advantages that have been discussed can be achieved independently in various embodiments or may be combined in yet other embodiments further details of which can be seen with reference to the following description and drawings.

BRIEF DESCRIPTION OF THE FIGURES

The novel features believed characteristic of the illustrative embodiments are set forth in the appended claims. The illustrative embodiments, however, as well as a preferred mode of use, further objectives and descriptions thereof, will best be understood by reference to the following detailed description of an illustrative embodiment of the present disclosure when read in conjunction with the accompanying drawings, wherein:

FIG. 8 shows a flowchart of an example method, according to an example embodiment.

FIG. 9 shows a flowchart of an example method for use with the method shown in FIG. 8, according to an example embodiment.

FIG. 10 shows a flowchart of an example method for use with the method shown in FIG. 8, according to an example embodiment.

FIG. 11 shows a flowchart of an example method for use with the method shown in FIG. 8, according to an example embodiment.

FIG. 12 shows a flowchart of an example method for use with the method shown in FIG. 8, according to an example embodiment.

DETAILED DESCRIPTION

Disclosed embodiments will now be described more fully hereinafter with reference to the accompanying drawings, in which some, but not all of the disclosed embodiments are shown. Indeed, several different embodiments may be described and should not be construed as limited to the embodiments set forth herein. Rather, these embodiments are described so that this disclosure will be thorough and complete and will fully convey the scope of the disclosure to those skilled in the art.

In use of a UV light source in ambient air that contains oxygen, certain wavelengths of UV light (particularly the Far UV wavelengths) can cause oxygen in the air to react and become ozone. Example systems and methods described herein temporarily displace the air that is in a path of the UV light, namely air that is proximal to the UV light source, while the UV light source is emitting UV light such that the UV light passes through substantially oxygen-depleted gas rather than ambient air, and therefore, reduces an opportunity for the creation of ozone. Because light energy is greater closer to the UV light source, ozone generation may have a higher chance of creation proximal to the UV light source, so air that is proximal to the UV light source can be displaced to mitigate ozone creation. In doing so, there is less or no need to mitigate the presence of ozone in confined spaces, particularly if proximal to humans or other things sensitive to ozone.

Existing solutions look to improved ventilation of the created ozone, and do not prevent creation of the ozone altogether. Example systems and methods described herein can reduce creation of ozone to improve safety and air quality in any areas (and specifically within enclosed areas such as on board an airplane), as well as remove undesirable ozone smell.

Figure 1:
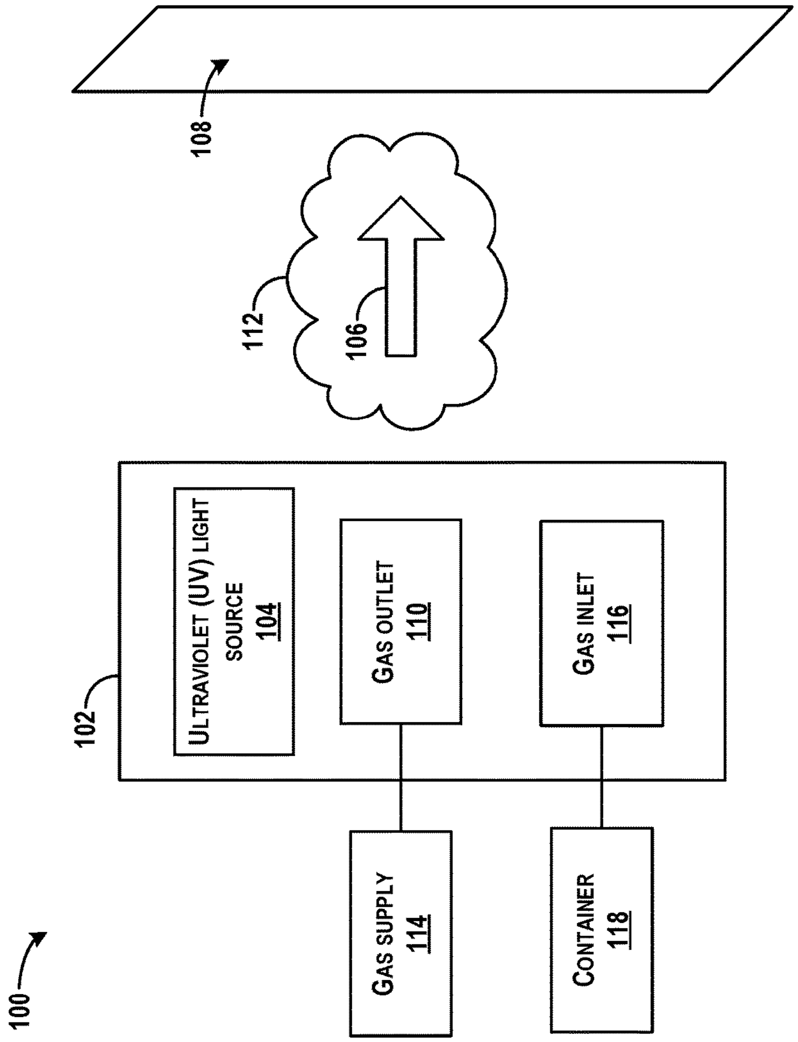
FIG. 1 is a block diagram of a system including an apparatus, according to an example embodiment.

Referring now to FIG. 1, a block diagram of a system 100 is illustrated, according to an example embodiment. The system 100 includes an apparatus 102 an ultraviolet (UV) light source 104 to direct UV light 106 onto an area 108, and a gas outlet 110 to disperse oxygen-depleted gas 112 over the UV light source 104, such that the UV light 106 passes through the oxygen-depleted gas 112 onto the area 108.

The UV light source 104 may take many forms, and examples include an excimer lamp, a light emitting diode (LED), a laser, or any combination of such light sources, or any other light source capable of producing a narrow band of light (e.g., within 10 nm) within or near the Far-UV spectrum. In addition, the UV light source 104 may include one light source, or multiple light sources arranged in any type of array as well in which the multiple light sources can be operated simultaneously and/or independently.

The UV light source 104 generates UV light that has wavelengths between about 100 nm to about 380 nm. In one example, the UV light source 104 is a 222 nm lamp.

The gas outlet 110 may include one or more ports for dispensing a gas. The gas outlet 110 can disperse the oxygen-depleted gas 112 over the area 108 to create a gas cloud, as shown in FIG. 1. In other examples, the gas outlet 110 can dispense gas as a focused jet of gas to direct the gas to a specific area.

The gas outlet 110 can be connected to a gas supply 114, which may be a container holding the gas. The gas can be any number of gases that contain little to no amounts of oxygen. In one example, the gas is oxygen-depleted gas. As some examples, the gas may be or include an inert gas. A specific example includes the gas as nitrogen, or at least including a majority percentage of nitrogen. Any inert gas will be effective to displace the air and fill an area proximal to the UV light source 104 with oxygen-depleted air. Nitrogen may be useful though since nitrogen is inexpensive and is already present in the air, and thus, is relatively safe.

The apparatus 102 also may include a gas inlet 116 to capture dispersed gas to a container 118. The gas inlet 116 can draw in the dispersed gas using a vacuum or other pressurized system.

The area 108 can be any area to be cleaned by the apparatus 102, and the apparatus 102 can be used to clean the area 108 by exposure to the UV light 106. In operation, the gas outlet 110 disperses the oxygen-depleted gas 112 over the area 108 so as to displace air that is in a path of the UV light 106 while the UV light source 104 is emitting the UV light 106. Displacing the air over the area 108 can mitigate formation of ozone gas due to the UV light 106 reacting with oxygen in the air.

Thus, within examples, the gas outlet 110 disperses the oxygen-depleted gas over the area 108 for a predetermined time period prior to operation of the UV light source 104 to direct the UV light 106 onto the area 108 so as to remove oxygen filled air from the UV light pathway. After the predetermined time period, the UV light source 104 can be operated to direct the UV light 106 to pass through the gas 112 onto the area 108. Because light is substantially instantaneous, and gas flow takes time, allowing the gas outlet 110 to disperse the oxygen-depleted gas first positions a gas cloud proximal to the UV light source 104 to have gas present when the UV light source 104 is turned on. Example operations are described below, and can include a short jet of the gas to coincide with a duty cycle of operation of the UV light source 104.

Because ozone gas is generated when oxygen filled air is exposed to UV light, removing the oxygen filled air from the pathway of the UV light will reduce creation of the zone gas. Many previous solutions increase ventilation of ozone gas generated from exposure to UV light; however, the apparatus 102 mitigates formation of ozone gas in the first instance. More specifically, if oxygen filled air is not present in the pathway of the UV light, then the ozone gas will not be formed.

The gas outlet 110 disperses nitrogen gas (or other inert or non UV light-reactive gases) over the UV light source 104 and/or over the area 108 resulting in the oxygen filled air being displaced, and then the UV light source can be operated to clean a surface of the area 108. There may be some instances (e.g., in flight use) where it would be desirable to recapture the nitrogen gas so that the dispersed gas does not remain in an enclosure (e.g., lavatory). In such an instance, the apparatus 102 can operate the gas inlet 116 to capture the nitrogen gas after the nitrogen gas has been dispersed on the area 108. In some other instances, the amount of nitrogen or inert or otherwise non-reactive gas is so small in comparison to ambient air in the enclosure, for example, that the overall composition of the ambient air is not significantly changed such that no recapture or other measures need to be taken in order to maintain high quality air.

The apparatus 102 may take many forms such as a handheld device, or a wall-mounted device.

Figure 2:
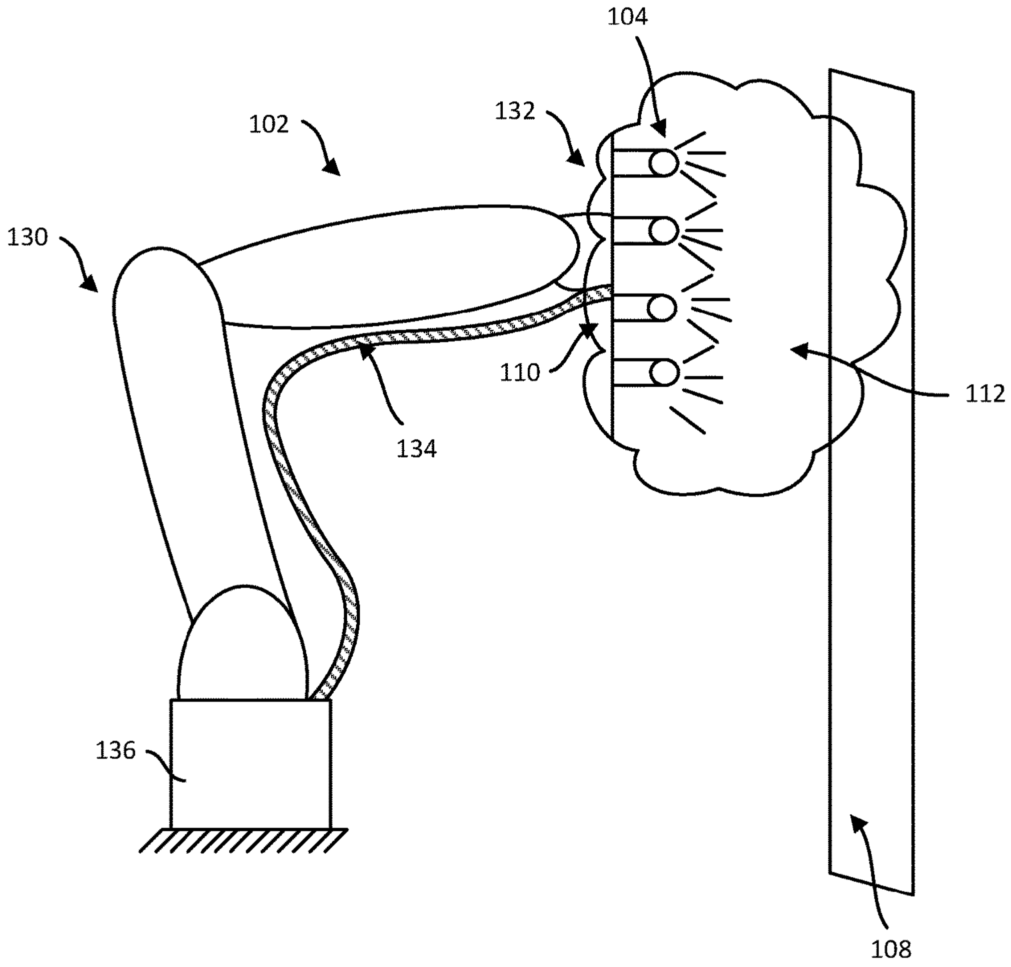
FIG. 2 is an illustration of the apparatus including a robotic arm, according to an example embodiment.

FIG. 2 is an illustration of the apparatus 102 including a robotic arm 130, according to an example embodiment. The gas outlet 110 and the UV light source 104 are mounted on the robotic arm 130, which can position the UV light source 104 and the gas outlet 110 over the area 108.

The robotic arm 130 may include an end effector 132 on which the gas outlet 110 and the UV light source 104 are mounted. The gas outlet 110 is shown to include a manifold attachment to dispense gas over a larger area, and specifically, to dispense gas over the UV light source 104. The UV light source 104 is shown as an array of lights.

Far-UV light, focused or not, is effective (at killing microbes) at closer distances, and it may also be more effective to have the nitrogen source near the UV light source 104 so that oxygen is displaced in areas proximal to the UV light source 104.

The gas outlet 110 can be connected to an umbilical cord 134 for a supply of the gas. The umbilical cord 134 can connect the gas supply 114 (shown in FIG. 1) to the gas outlet 110. In an example where the system and/or the apparatus is included on an aircraft, the gas supply 114 may include or be connected to an on-board inert gas system available on the aircraft for inerting fuel tanks, for example.

The robotic arm 130 may have any number of joints to provide multiple degrees of freedom (DOF), and can be connected to a base 136 that is mounted to a stationary component, such as a wall.

In one example, the apparatus 102 is automated so that the robotic arm 130 positions the UV light source 104 and the gas outlet 110 over or proximal to the area 108 to be cleaned.

In another example, the apparatus 102 including the robotic arm 130 is not static, and can be moved from place to place so as to clean multiple surfaces and/or larger area.

The system 100 and/or the apparatus 102 may be included within a number of different vehicles, including aircraft, automobiles, or boats, for example, or within a number of different areas, such as hospitals, manufacturing plants, or residential homes.

As one example, the apparatus 102 is positioned in a lavatory on an aircraft, and the UV light source 104 operates to emit UV light when the lavatory is not in use. In addition, the gas outlet 110 disperses the oxygen-depleted gas over the area 108 in the lavatory so as to displace air that is in a path of the UV light while the UV light source 104 is emitting the UV light. Operation of the apparatus 102 can be triggered based on detection that the lavatory is not in use, such as closing the door, or turning off the light in the lavatory. Alternatively, the apparatus 102 can be manually operated.

In the example where the apparatus 102 is used for cleaning an area in a lavatory for in service flights, the apparatus 102 may be operated after every use of the lavatory. The robotic arm 130 may be mounted on a wall of the lavatory, and when the lavatory empty and not in use, the apparatus 102 activates. The UV light source 104 may be operated for less than ten seconds to clean an area, and in some example, within 3-5 seconds. Since the UV light source 104 is operated in an enclosed space, the creation of ozone is undesirable, and the apparatus 102 can be used to reduce creation of ozone.

Figure 3:
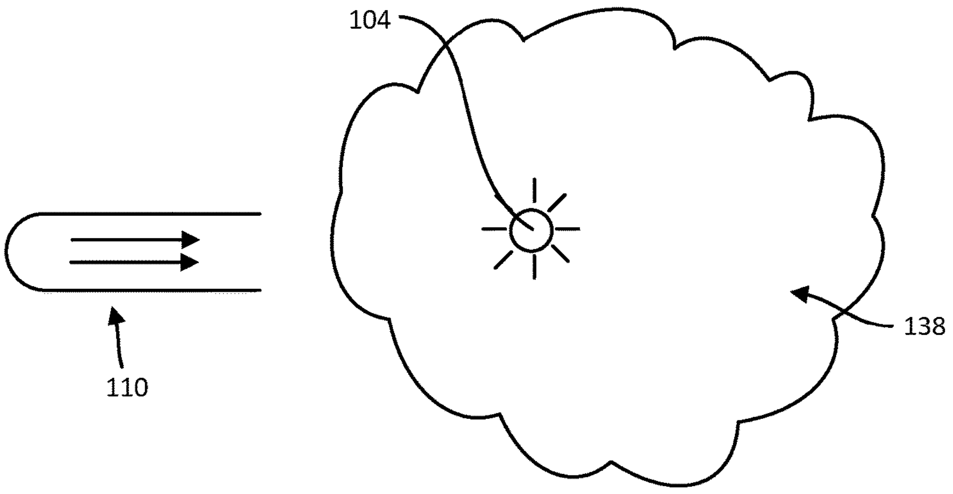
FIG. 3 illustrates a portion of the apparatus and an example operation of the apparatus, according to an example embodiment.

As mentioned, to reduce creation of ozone, the gas outlet 110 dispenses gas over the UV light source 104. FIG. 3 illustrates a portion of the apparatus 102 and an example operation of the apparatus 102, according to an example embodiment. In FIG. 3, the gas outlet 110 dispenses an inert gas over the UV light source 104 for a predetermined time period prior to operation of the UV light source 104. Once a gas cloud 138 is created (e.g., an oxygen-depleted gas cloud) after passage of the predetermined time period, the UV light source 104 is operated to direct the UV light to pass through the inert gas onto the area 108. Thus, a time delay method of operation can be used to start flow of the gas prior to turning on the UV light source 104 to perhaps reach a certain minimal oxygen concentration or steady state gas flow prior to turning on the UV light source 104, for example. The UV light source 104 can be turned on when the gas cloud 138 is formed and turned off as the gas cloud 138 dissipates.

In some examples, the gas outlet 110 may stop dispensing the gas once the gas cloud 138 is formed. In other examples, the gas outlet 110 may dispense gas continuously until the UV light source 104 is turned off.

Figure 4:
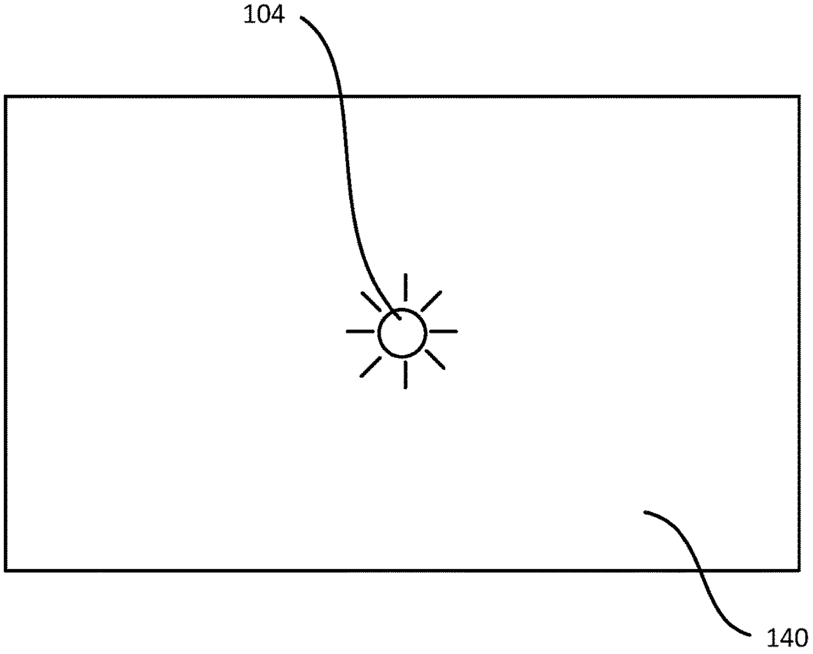
FIG. 4 illustrates a portion of the apparatus and another example operation of the apparatus, according to an example embodiment.

FIG. 4 illustrates a portion of the apparatus 102 and another example operation of the apparatus 102, according to an example embodiment. FIG. 4 illustrates a method of operation in which the UV light source 104 is bathed or immersed in an oxygen-depleted environment 140. The oxygen-depleted environment may not require an active nitrogen source, but rather, the UV light source 104 is contained or enclosed in the oxygen-depleted environment 140. The oxygen-depleted environment 140 may include or be filled with nitrogen. Here, the oxygen-depleted environment 140 may be a small enclosure surrounding the UV light source 104, for example, and all light emitted from the UV light source 104 passes through the oxygen-depleted environment 140 for application to the area 108.

Figure 5:
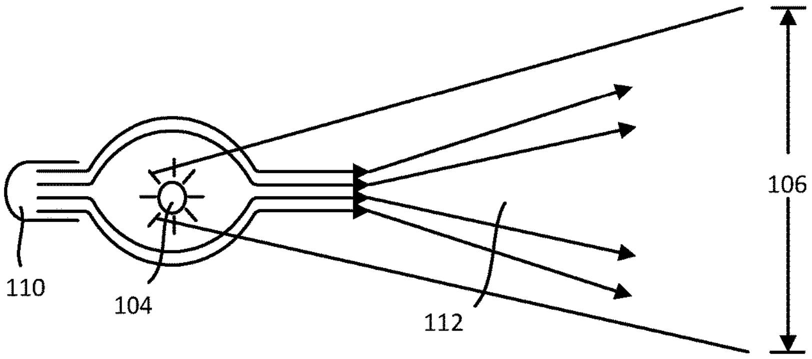
FIG. 5 illustrates a portion of the apparatus and another example operation of the apparatus, according to an example embodiment.

FIG. 5 illustrates a portion of the apparatus 102 and another example operation of the apparatus 102, according to an example embodiment. In FIG. 5, the gas outlet 110 is positioned behind the UV light source 104, and the gas outlet 110 disperses the oxygen-depleted gas 112 over the UV light source 104 and in parallel to the UV light 106.

Figure 6:
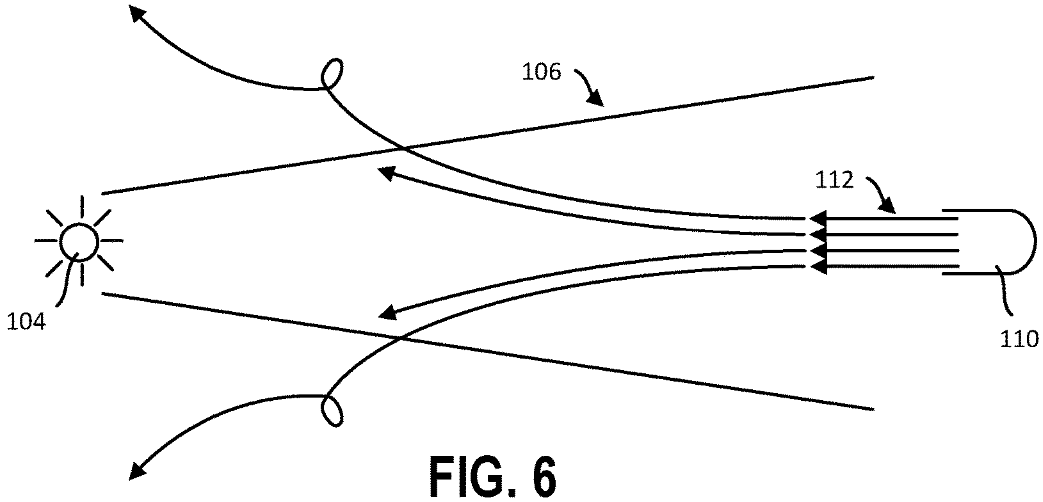
FIG. 6 illustrates a portion of the apparatus and another example operation of the apparatus, according to an example embodiment.

FIG. 6 illustrates a portion of the apparatus 102 and another example operation of the apparatus 102, according to an example embodiment. In FIG. 6, the UV light source 104 is positioned to face the gas outlet 110, and the gas outlet 110 is positioned to face the UV light source 104. The gas outlet 110 then disperses the oxygen-depleted gas toward the UV light source 104, and the UV light source 104 directs the UV light toward the gas outlet 110. Gas flows counter to the light beam in the example shown in FIG. 6.

Figure 7:
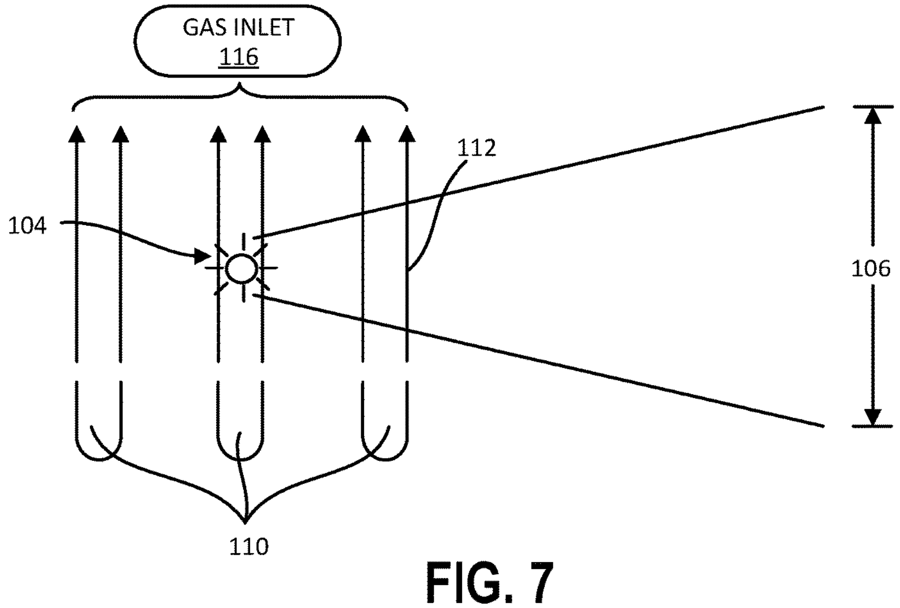
FIG. 7 illustrates a portion of the apparatus and another example operation of the apparatus, according to an example embodiment.

FIG. 7 illustrates a portion of the apparatus 102 and another example operation of the apparatus 102, according to an example embodiment. In FIG. 7, the gas outlet 110 is configured to disperse the oxygen-depleted gas 112 perpendicular to the UV light 106 of the UV light source 104. The gas inlet 116 may be positioned to remove or collect the dispersed gas.

Within many of the example configurations illustrated in the figures, the flow of oxygen-depleted gas is over the UV light source 104. In other examples, the flow of oxygen-depleted gas may be in close proximity to the UV light source 104 since light is at a highest intensity at the UV light source 104. Because light is at a highest intensity at the UV light source 104, the oxygen-depleted gas will have a maximum effect of blocking a reaction of UV light with any oxygen so as to reduce creation of ozone. However, generally, the oxygen-depleted gas may be focused on any desired area where the UV light source 104 will be directed.

In the examples shown in FIGS. 5-7, the oxygen-depleted gas 112 is co-located with the UV light 106, and the gas outlet 110 may disperse the oxygen-depleted gas 112 over the UV light source 104 for temporary amount of time (not continuously).

FIG. 8 shows a flowchart of an example method 200, according to an example embodiment. Method 200 shown in FIG. 8 presents an embodiment of a method that could be used with the system 100 shown in FIG. 1 and the apparatus 102 shown throughout the figures, for example. Further, devices or systems may be used or configured to perform logical functions presented in FIG. 8. In some instances, components of the devices and/or systems may be configured to perform the functions such that the components are actually configured and structured (with hardware and/or software) to enable such performance. In other examples, components of the devices and/or systems may be arranged to be adapted to, capable of, or suited for performing the functions, such as when operated in a specific manner. Method 200 may include one or more operations, functions, or actions as illustrated by one or more of blocks 202 and 204. Also, the various blocks may be combined into fewer blocks, divided into additional blocks, and/or removed based upon the desired implementation.

It should be understood that for this and other processes and methods disclosed herein, flowcharts show functionality and operation of one possible implementation of present embodiments. Alternative implementations are included within the scope of the example embodiments of the present disclosure in which functions may be executed out of order from that shown or discussed, including substantially concurrent or in reverse order, depending on the functionality involved, as would be understood by those reasonably skilled in the art.

At block 202, the method 200 includes dispersing, by the gas outlet 110, oxygen-depleted gas 112 over the UV light source 104. At block 204, the method 200 includes directing the UV light 106 from the UV light source 104 to pass through the oxygen-depleted gas 112 onto the area 108.

As described in examples above, the oxygen-depleted gas 112 can be dispersed parallel to the light beam 106 of the UV light source 104, perpendicular to the light beam 106 of the UV light source 104, or toward the UV light source 104.

In addition, the oxygen-depleted gas 112 can be dispersed over the area 108 to create a gas cloud 138, and subsequently, the UV light source 104 can be operated to direct the UV light 106 onto the area 108.

FIG. 9 shows a flowchart of an example method for use with the method 200, according to an example embodiment. At block 206, functions include dispersing the oxygen-depleted gas 112 over the UV light source 104 for a predetermined time period prior to operation of the UV light source 104 to direct the UV light 106 onto the area 108.

FIG. 10 shows a flowchart of an example method for use with the method 200, according to an example embodiment. At block 208, functions include capturing, by the gas inlet 116, dispersed oxygen-depleted gas into the container 118.

FIG. 11 shows a flowchart of an example method for use with the method 200, according to an example embodiment. The gas outlet 110 and the UV light source 104 can be positioned in a lavatory on an aircraft, and in this example configuration, at block 210, functions include operating the UV light source 104 to emit the UV light 106 onto the area 108 when the lavatory is not in use. At block 212, functions include dispersing the oxygen-depleted gas 112 over the area 108 so as to displace air that is in a path of the UV light 106 while the UV light source 104 is emitting the UV light 106.

FIG. 12 shows a flowchart of an example method for use with the method 200, according to an example embodiment. At block 214, functions include displacing air over the area 108 to mitigate formation of ozone gas due to the UV light 106 reacting with oxygen in the air.

Figure 13:
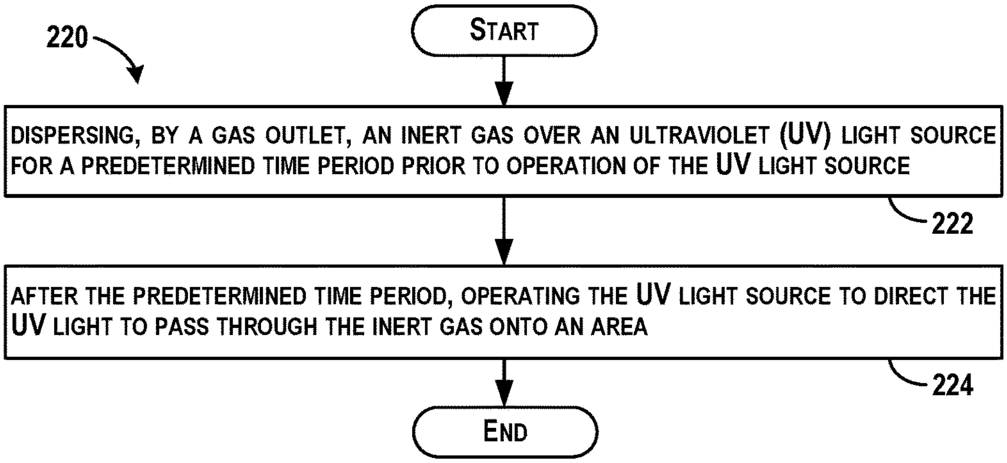
FIG. 13 shows a flowchart of another example method, according to an example embodiment.

FIG. 13 shows a flowchart of another example method 220, according to an example embodiment. Method 220 shown in FIG. 13 presents an embodiment of a method that could be used with the system 100 shown in FIG. 1 and the apparatus 102 shown throughout the figures, for example. Further, devices or systems may be used or configured to perform logical functions presented in FIG. 13. Method 220 may include one or more operations, functions, or actions as illustrated by one or more of blocks 222 and 224. Also, the various blocks may be combined into fewer blocks, divided into additional blocks, and/or removed based upon the desired implementation.

At block 222, the method 220 includes dispersing, by the gas outlet 110, an inert gas over the UV light source 104 for a predetermined time period prior to operation of the UV light source 104. At block 224, the method 220 includes after the predetermined time period, operating the UV light source 104 to direct the UV light 106 to pass through the inert gas onto the area 106.

Figure 14:
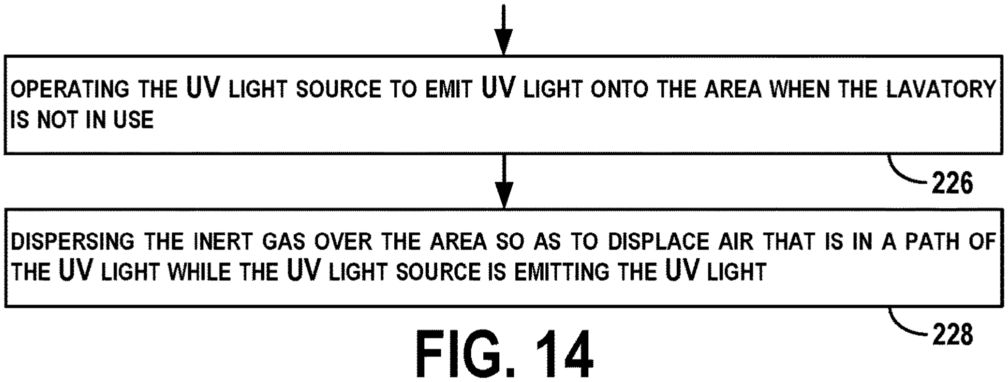
FIG. 14 shows a flowchart of an example method for use with the method shown in FIG. 13, according to an example embodiment.

FIG. 14 shows a flowchart of an example method for use with the method 220, according to an example embodiment. Similar to examples above, the gas outlet 110 and the UV light source 104 are positioned in a lavatory on an aircraft, and at block 226, functions include operating the UV light source 104 to emit the UV light 106 onto the area 108 when the lavatory is not in use. At block 228, functions include dispersing the inert gas over the area 108 so as to displace air that is in a path of the UV light 106 while the UV light source 104 is emitting the UV light 106.

The description of the different advantageous arrangements has been presented for purposes of illustration and description, and is not intended to be exhaustive or limited to the embodiments in the form disclosed. Many modifications and variations will be apparent to those of ordinary skill in the art. Further, different advantageous embodiments may describe different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method comprising:

dispersing, by a gas outlet, oxygen-depleted gas over an ultraviolet (UV) light source, wherein dispersing the oxygen-depleted gas over the UV light source comprises dispersing the oxygen-depleted gas toward the UV light source; and directing UV light from the UV light source to pass through the oxygen-depleted gas onto an area, wherein directing the UV light from the UV light source to pass through the oxygen-depleted gas comprises directing the UV light toward the gas outlet.

2. The method of claim 1, wherein the oxygen-depleted gas comprises an inert gas.

3. The method of claim 1, wherein dispersing the oxygen-depleted gas over the UV light source comprises:

dispersing the oxygen-depleted gas over the area to create a gas cloud; and subsequently operating the UV light source to direct the UV light onto the area.

4. The method of claim 1, further comprising:

dispersing the oxygen-depleted gas over the UV light source for a predetermined time period prior to operation of the UV light source to direct the UV light onto the area.

5. The method of claim 1, further comprising:

capturing, by a gas inlet, the dispersed oxygen-depleted gas into a container.

6. The method of claim 1, wherein the gas outlet and the UV light source are positioned in a lavatory on an aircraft, and wherein the method further comprises:

operating the UV light source to emit the UV light onto the area when the lavatory is not in use; and dispersing the oxygen-depleted gas over the area so as to displace air that is in a path of the UV light while the UV light source is emitting the UV light.

7. The method of claim 1, further comprising:

displacing air over the area to mitigate formation of ozone gas due to the UV light reacting with oxygen in the air.

8. A method comprising:

dispersing, by a gas outlet, an inert gas over an ultraviolet (UV) light source for a predetermined time period prior to operation of the UV light source, wherein dispersing the inert gas over the UV light source comprises dispersing the inert gas toward the UV light source; and after the predetermined time period, operating the UV light source to direct UV light to pass through the inert gas onto an area, wherein directing the UV light from the UV light source to pass through the inert gas comprises directing the UV light toward the gas outlet.

9. The method of claim 8, wherein the gas outlet and the UV light source are positioned in a lavatory on an aircraft, and wherein the method further comprises:

operating the UV light source to emit the UV light onto the area when the lavatory is not in use; and dispersing the inert gas over the area so as to displace air that is in a path of the UV light while the UV light source is emitting the UV light.

10. The method of claim 8, further comprising:

dispersing the inert gas over the UV light source for a predetermined time period prior to operation of the UV light source to direct the UV light onto the area.

11. The method of claim 8, further comprising:

capturing, by a gas inlet, the dispersed inert gas into a container.

12. A method comprising:

dispersing, by a gas outlet, oxygen-depleted gas over an ultraviolet (UV) light source so as to displace air that is in a path of UV light emitted by the UV light source while the UV light source is emitting the UV light, wherein the gas outlet and the UV light source are positioned in a lavatory on an aircraft; and operating the UV light source to emit the UV light onto an area when the lavatory is not in use.

13. The method of claim 12, wherein dispersing the oxygen-depleted gas over the UV light source comprises dispersing the oxygen-depleted gas parallel to a light beam of the UV light.

14. The method of claim 12, wherein dispersing the oxygen-depleted gas over the UV light source comprises dispersing the oxygen-depleted gas perpendicular to a light beam of the UV light.

15. The method of claim 12, wherein the oxygen-depleted gas comprises an inert gas.

16. The method of claim 12, further comprising:

dispersing the oxygen-depleted gas over the UV light source for a predetermined time period prior to operation of the UV light source to direct the UV light onto the area.

17. The method of claim 12, further comprising:

capturing, by a gas inlet, the dispersed oxygen-depleted gas into a container.

18. The method of claim 12, further comprising:

displacing air over the area to mitigate formation of ozone gas due to the UV light reacting with oxygen in the air.

* * * * *